(12) United States Patent
Ashkinazi

(10) Patent No.: US 10,299,480 B2
(45) Date of Patent: May 28, 2019

(54) ANTIVIRAL AGENT

(71) Applicants: Viktor Veniaminovich Tets, Saint Petersburg (RU); Georgy Viktorovich Tets, Saint Petersburg (RU)

(72) Inventor: Rimma Ilinichna Ashkinazi, Saint Petersburg (RU)

(73) Assignees: VIKTOR VENIAMINOVICH TETS, St. Petersburg (RU); GEORGY VIKTOROVICH TETS, St. Petersburg (RU)

(*) Notice: Subject to any disclaimer, the term of this patent is extended or adjusted under 35 U.S.C. 154(b) by 0 days.

(21) Appl. No.: 15/124,289

(22) PCT Filed: Dec. 10, 2014

(86) PCT No.: PCT/RU2014/000917
§ 371 (c)(1),
(2) Date: Sep. 7, 2016

(87) PCT Pub. No.: WO2015/133928
PCT Pub. Date: Sep. 11, 2015

(65) Prior Publication Data
US 2017/0013838 A1 Jan. 19, 2017

(30) Foreign Application Priority Data
Mar. 7, 2014 (RU) ................. 2014109125

(51) Int. Cl.
*A01N 47/44* (2006.01)
*A61K 31/785* (2006.01)
*C08G 73/02* (2006.01)
*C07C 281/16* (2006.01)

(52) U.S. Cl.
CPC ............ *A01N 47/44* (2013.01); *A61K 31/785* (2013.01); *C07C 281/16* (2013.01); *C08G 73/02* (2013.01); *C08G 2310/00* (2013.01)

(58) Field of Classification Search
CPC .............................. A01N 47/44; A61K 31/785
See application file for complete search history.

(56) References Cited

U.S. PATENT DOCUMENTS

| 8,993,712 | B2 | 3/2015 | Tets et al. |
| 2002/0010150 | A1 | 1/2002 | Cortese et al. |
| 2004/0082925 | A1 | 4/2004 | Patel |
| 2006/0079503 | A1 | 4/2006 | Schwede et al. |
| 2011/0269936 | A1* | 11/2011 | Tets ............... A61K 31/155 528/422 |
| 2013/0096062 | A1 | 4/2013 | Hedrich et al. |
| 2013/0150451 | A1 | 6/2013 | Salamone et al. |
| 2014/0023714 | A1 | 1/2014 | Gagnieu et al. |

FOREIGN PATENT DOCUMENTS

| CN | 102453315 A | 5/2012 |
| CN | 103705535 A | 4/2014 |
| RU | 2039735 C1 | 7/1995 |
| RU | 2141452 C1 | 11/1999 |
| RU | 2176523 C2 | 12/2001 |
| RU | 2176651 C2 | 12/2001 |
| RU | 2230734 C1 | 6/2004 |
| RU | 2004135533 A | 7/2005 |
| RU | 2006122738 A | 1/2008 |
| RU | 2324478 C2 | 5/2008 |
| RU | 2422137 C1 | 6/2011 |
| RU | 2423359 C1 | 7/2011 |
| RU | 2480227 C2 | 4/2013 |
| RU | 2533232 C2 | 1/2014 |
| RU | 2012130924 A | 1/2014 |
| RU | 2546006 C1 | 4/2015 |
| WO | 96/28570 A1 | 9/1996 |
| WO | 99/18232 A1 | 4/1999 |
| WO | 2001082937 A1 | 11/2001 |
| WO | 20030093249 A1 | 11/2003 |
| WO | 2008008912 A1 | 1/2008 |

(Continued)

OTHER PUBLICATIONS

Extended European Search Report Issued in European Application No. 16167120.1 dated Oct. 27, 2016, 6 pages.
Supplementary European Search Report dated Nov. 20, 2013, from corresponding European Application No. 10822298.5, 3 pages.
Translation of the International Preliminary Report on Patentability dated Apr. 11, 2012 from corresponding International Application No. PCT/RU2010/000292, 4 pages.
Translation of the International Search Report and Written Opinion of the Interanational Searching Authority dated Oct. 28, 2010, from corresponding International Application No. PCT/RU2010/000292, 11 pages.
Wei, Dafu et al., "Structural characterization and antibacterial activity of oligoguanidine (polyhexamethylene guanidine hydrochloride)", Materials Science and Engineering C 29 (2009), pp. 1776-1780.

(Continued)

Primary Examiner — Jospeh R Kosack
(74) Attorney, Agent, or Firm — Troutman Sanders LLP

(57) ABSTRACT

The invention relates to antiviral agents and specifically to synthetic biologically-active derivatives, and can be used in the pharmaceutical industry, in medicine, in plant husbandry and in biotechnology. The antiviral agent is based on poly-N1-hydrazino(imino)methyl-1,6-hexanediamine-poly-N1-amino(imino)methyl-1,6-hexane diamine of general formula (1),

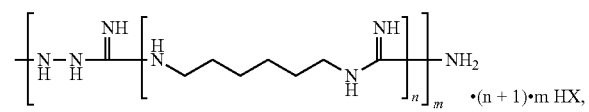

where: HX is an acid, n=3-20, and m=4-20, and which is active against viruses of humans, animals, plants, bacteria and fungi, said viruses being non-enveloped and enveloped and containing RNA or DNA. The antiviral agent exhibits a broad range of effectiveness, and is active against viruses both in intracellular and extracellular locations.

20 Claims, No Drawings

(56) References Cited

FOREIGN PATENT DOCUMENTS

| WO | 2011/135577 A1 | 11/2011 |
| WO | 2013053753 A2 | 4/2013 |
| WO | 2016118043 A1 | 7/2016 |

OTHER PUBLICATIONS

Denton, G.W. (1991) Chlorhexidine. In: Block, S.S., Ed., Disinfction, Sterization, Preservations, 4 Edition, Lea & Fegiber, Philadelphia, 274-289.

Journal of Clinical Pathology 1972, vol. 25 76-78.

International Search Report and Written Opinion Issued in International Application No. PCT/RU2014/000917 dated Apr. 29, 2015 and English Language Translation Thereof, 7 pages.

European Extended Search Report Issued in European Patent Application No. 13853343.5 for PCT/RU2013/000394 dated Jun. 6, 2016, 6 pages.

Extended European Search Report Issued in European Patent Application No. 14884461.6, dated Aug. 2, 2017, 8 pages.

International Search Report and Written Opinion Issued in International Application No. PCT/RU2015/000253, dated Sep. 10, 2015 and English Translation Thereof, 10 pages.

Lysytsya A., et al., "The Antiviral Action of Polyhexamethylene Guanidine Derivatives", Journal of Life Sciences (2014), vol. 8, No. 1, pp. 22-26.

European Extended Search Report Issued in European Patent Application No. 10822298.5 for PCT/RU2010/000292, dated Nov. 20, 2013, 3 pages.

Translation of the International Preliminary Report on Patentability dated Sep. 13, 2016 from corresponding International Application No. PCT/RU2014/000917, 5 pages.

Communication (International Search Report and Written Opinion) issued by the International Searching Authority in International Patent Application No. PCT/US2018/033880, dated Sep. 20, 2018, 11 pages total.

Communication (Extended European Search Report) issued by the European Patent Office in European Patent Application No. 15879124.1, dated Sep. 20, 2018, 6 pages total.

* cited by examiner

ANTIVIRAL AGENT

CROSS-REFERENCE TO RELATED APPLICATIONS

This application is a U.S. National Phase of International Patent Application No. PCT/RU2014/000917, filed Dec. 10, 2014, which claims priority to Russian Application No. 2014109125, filed Mar. 7, 2014, both of which applications are herein incorporated by reference in their entirety.

FIELD

The invention relates to antiviral agents and specifically to synthetic biologically-active derivatives, and can be used in the pharmaceutical industry, in medicine, in plant husbandry and in biotechnology.

The present substance is active against enveloped and non-enveloped viruses containing RNA or DNA, and is capable to inactivate these viruses both in intracellular and extracellular locations.

Viral infections are one of the most serious problems of modern medicine. For most viral infections there are either no treatments, or they are extremely difficult to treat. This is due to lack of efficiency of existing drugs and variability of pathogens, leading to the emergence of resistant forms. Similar problems are relevant for veterinary medicine and agriculture. There are even fewer drugs active against viruses in extracellular locations, which is due to the complete absence of metabolism in viruses, which is the main target of antimicrobial drugs.

Viruses consisting of organic molecules are not living organisms, have no cellular structure, no metabolism, which makes them extremely resistant to various impacts, including chemicals and pharmaceuticals.

The number of viruses that cause diseases in humans, animals and plants is continuously increasing, mainly due to improvement of the methods for their detection and due to their spread resulting from human economic activity (development of new territories, mainly in Africa) and the formation of new variations of the known viruses (variability of influenza viruses, etc.). The number of commonly available antiseptics for industry, medicine, veterinary medicine and agriculture is clearly insufficient. Most of the existing drugs have a number of significant shortcomings, and, above all, toxicity, odor, low efficiency. Formation and spread of resistant viral clones is observed. All of the above increases the timeliness of creating new drugs active against viral particles.

It is known that some disinfectants are capable to inactivate viruses, but due to their relatively high toxicity they cannot be used directly in humans. There is a solution with antiviral activity at relatively low toxicity—Chlorhexidine digluconate (CHX). There are controversial evidences from different authors on the effects of CHX on different viruses both in their range and the exposure time. In this vein, it is indicated that CHX is only active against enveloped viruses with an additional lipid-protein shell (Denton G. W. 1991. Chlorhexidine, p. 274-289. In Block S. S. (ed), Disinfection, sterilization and preservation, 4th ed. Lea and Fibiger, Philadelphia, Pa. J. Clin. Path., 1972, 25, 76-78.

CHX is effective against the herpes virus at a 10 minute exposure, reducing the number of its particles by 5-6 times and in the same conditions, had virtually no effect on non-enveloped viruses, deprived of the additional shell, adenovirus and poliovirus. There is no reliable data on CHX activity against bacteria viruses—bacteriophages. Despite the obvious disadvantages, CHX is currently the most common means of action upon virus particles for the purpose of their inactivation.

BACKGROUND

There is a commonly known antiviral agent based on melanin, containing soluble melanin at a concentration of 0.002 mg/ml to 25 mg/ml obtained by extraction from basidiomycete Inonotus obliquus and possessing antiviral activity against viruses of influenza, herpes simplex type 2, immunodeficiency (HIV 1) and vaccinia, RU 2480227, publ. 27 Apr. 2013.

The disadvantage of this solution is a narrow range of activity.

There is another commonly known antiviral agent based on fullerene derivative $C_{60}$ KB-517, having the following structural formula

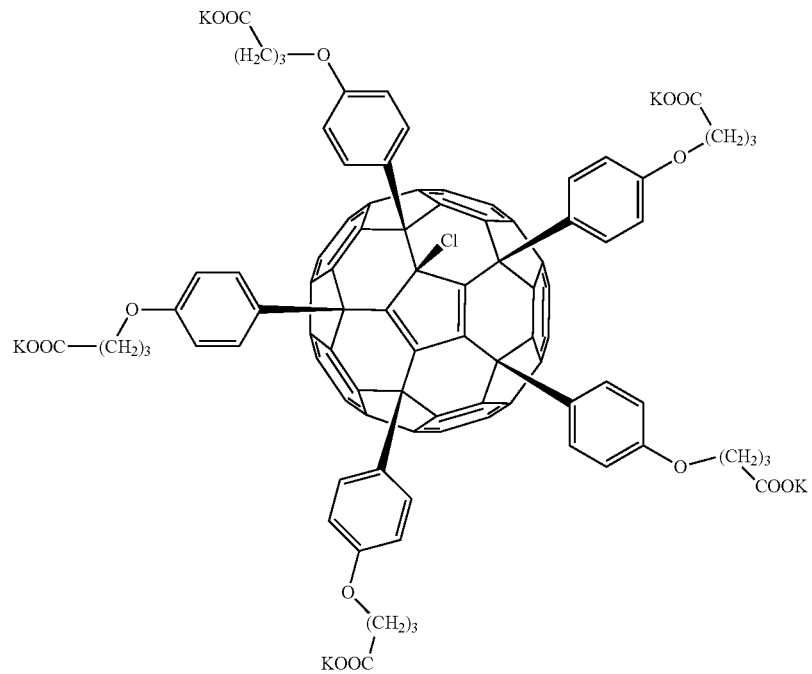

as a microbicide antiviral agent for inhibition of the herpes simplex virus and cytomegalovirus, RU 2012130924 A, publ. 27 Jan. 2014.

The efficiency of this solution is very low; presumably, it can be used for prophylaxis.

There is another commonly known antiviral agent with the following general structural formula:

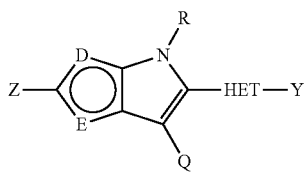

where Y is selected from the group consisting of aryl, heteroaryl, substituted aryl and substituted heteroaryl;
HET is selected from the group consisting of a six-membered arylene cycle, six-membered heteroarylene cycle containing one, two or three heteroatoms selected from N, O or S, WO 2008008912 A1, publ. 17 Jan. 2008.

This solution is substantially active against Flaviviridae family of viruses only that cause cirrhosis and liver cancer in humans and animals.

The closest to the claimed solution in terms of structure is an antiviral agent, which, as well as the present one, contains hydrazine groups and carbonyl fragments: an antiviral agent on the basis of 4-{3.5-Dioxo-4-azatetracyclo[5.3.2.0$^{2,6}$0.0$^{8,10}$] dodec-11-en-4-yl}-4-azatetracyclo [5.3.2.0$^{2,6}$0.0$^{8,10}$] dodec-11-ene-3.5-dione of the following formula:

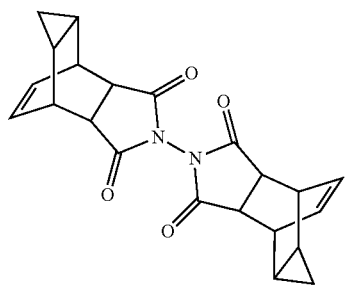 [SMILES: O=C1C2C3C=CC(C4CC34)C2C(=O)N1N1C(=O)C2C3C=CC(C4CC34)C2C1=O]

which is active against orthopoxviruses pathogen for humans and animals, RU 2423359 C1, publ. 10 Jul. 2011.

Its disadvantage, as the above analogs, is narrow spectrum of activity, low efficiency, especially against viruses in a free extracellular location.

SUMMARY OF THE INVENTION

It is an object of the present invention to provide a broad-spectrum antiviral agent active against viruses in both intracellular and extracellular positions.

According to the invention, the problem is solved by means of an antiviral agent on the basis of poly-N1-hydrazino(imino)-methyl-1,6-hexanediamine-poly-N1-amine (imino)-methyl-1,6-hexanediamine of the general formula:

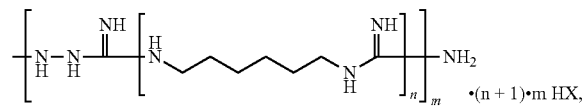

where: HX—acid, n=3-20, m=4-20, active against enveloped and non-enveloped viruses containing RNA or DNA in humans, animals, plants, bacteria and fungi.

When n×m<12, the drug activity is insufficient, when n×m>400 the substance becomes poorly soluble in water and biological fluids and therefore ineffective.

The applicant has not found any technical solutions identical to the present invention, which enables to conclude that the invention meets to the "Novelty" (N) criterion for patentability.

Implementation of the present invention features provides an extension of the antiviral agent's spectrum of activity, as well as its activity against viruses in both intracellular and extracellular positions.

The applicant has not found any sources of information containing data on the impact of the claimed distinguishing features on the technical effect occurred due to implementation thereof, which, in the applicant's opinion, enables to conclude that the invention meets to the "Inventive Step" ("IS") criterion for patentability.

BRIEF DESCRIPTION OF DRAWINGS

The invention is further explained by way of detailed description of examples of its embodiments, without any references to drawings.

PREFERRED EMBODIMENT

Examples of Preparation of the Antiviral Agent

Example 1 n=5, m=6.

A three-necked 1 liter flask equipped with an inert gas supply tube, a thermometer and a gas outlet tube, were charged with 95.5 g (1 mole) of iminourea hydrochloride (also known as guanidine hydrochloride) (46.8 wt. %), 103.4 g (0.89 mol) of 1.6-diaminohexane (DH) (50.7 wt. %), and 5 g (0.1 mole) of hydrazine hydrate, after which the flask was purged with nitrogen. The contents of the flask were stirred and placed into an air bath, while the gas outlet tube was connected to the ammonia catchment receiver. Then, while purging with nitrogen at a rate of 30-40 ml/min, the reaction mixture was heated with gradual removal of water and ammonia over 1 hour adjusting the temperature of the mass to the constant reaction temperature of 190° C. The reaction was aged for 30 minutes, while the system was purged with nitrogen. At this point, the system was cooled to 160° C. and the hot syrupy mixture was poured onto a metal pan and cooled to obtain 169.9 of the product as a solid, almost colorless transparent vitrifaction.

Example 2

The antiviral agent was prepared analogously to Example 1, with n=10, m=10, DH=0.50 mole, HH=0.1 mole. The reaction temperature and the holding time values are given in Table 1.

Example 3

The substance was prepared analogously to Example 1, with n=28, m=20, DH=1.8 mole, HH=0.1 mole, the reaction temperature and the holding time values are given in Table 1.

The resulting polymer is non-stereoregular, i.e. the mutual arrangement of alternating components of hydrazine and 1.6-diamine-hexane in the polymer chain may be arbitrary. But the average proportion of these components determined by the proportion of the initial reagents has a constant value in each example.

The antiviral agent substance has a nanostructure.

The nanostructure is determined by the methods of dynamic light scattering using a Malvern Instruments Nanosizer Nano-ZS particle size analyzer and a FEI Tecnai G212Cryo12 transmission electron microscope configured to cool the samples to the boiling point of liquid nitrogen.

Using the dynamic light scattering method it was found that the solution contains globules having the size of 10-15 nm at the preparation concentration of 0.05 mg/ml. An electron-microscopic examination also revealed globules having the size of 10-15 nm.

The following are examples of application of the present antiviral agent.

Example 1

The study of antiviral action on a non-enveloped RNA containing poliovirus that causes poliomyelitis belonging to the Picornaviridae family causing human diseases.

The antiviral agent was used in the form of a 1.0% aqueous solution. The virus dwell time with the solution was 0.5-2.0 minutes at the temperature of 20±2° C.

Human viruses were grown in cell culture. Antiviral activity was determined by the method of inactivation on the surface of artificial leather. A neutralizer (bovine serum) was used in the experiments. Virus replication in the cells was evaluated by virus-induced cytopathic effect by the degree of inhibition of the infectious virus titer, measured in lg $TCID_{50}$ (50% tissue cytopathic infectious dose). To work with the poliomyelitis virus a passaged culture of kidney cells of green monkey Vero was used.

The findings on virucidal activity of the solution during treatment of the test objects infected with poliomyelitis virus with a 1.0% solution of the antiviral agent, are presented in Table 2.

Thus, the antiviral agent exhibits virucidal activity against non-enveloped virus containing RNA.

Example 2

The study of antiviral action of the antiviral agent on non-enveloped DNA containing adenoviruses. Adenoviruses of various serotypes cause infectious diseases in humans and animals (cattle, birds, sheep, dogs). The infectious diseases in animals caused by adenoviruses are characterized by lesions of the mucous membranes of the respiratory organs, intestines, eyes and lymphoid tissue.

To work with the adenovirus the transplantable human cell line HeLa was used. The reproduction of viruses in cells was evaluated by virus-induced cytopathic effect by the degree of inhibition of the infectious virus titer, measured in lg $TCID_{50}$.

The antiviral agent was used in the form of a 0.5% aqueous solution. The virus dwell time with the solution was 0.5-2.0 minutes at the temperature of 20±2° C.

The findings on virucidal activity of the antiviral solution during treatment of the test objects infected with adenoviruses with a 0.5% solution, are presented in Table 3.

Thus, the tested antiviral solution exhibits virucidal activity against non-enveloped DNA-containing adenoviruses of humans and animals.

Example 3

The study of antiviral action of the antiviral agent on enveloped DNA containing herpes simplex viruses. Herpes viruses of various serotypes cause infectious diseases in humans and animals. Infections of these viruses manifest in lesions of mucosae, skin, malignant transformation of cells.

To work with the herpes virus a passaged culture of kidney cells of green monkey Vero was used. The virus reproduction in cells was evaluated by virus-induced cytopathic effect by the degree of inhibition of the infectious virus titer, measured in lg $TCID_{50}$.

The antiviral agent was used in the form of a 1.0% aqueous solution. The virus dwell time with the solution was 0.5-4.0 minutes at the temperature of 20±2° C.

The findings on virucidal activity of the antiviral solution during treatment of the test objects infected with herpes simplex virus with a 1.0% solution, are presented in Table 4.

Thus, the tested antiviral solution exhibits virucidal activity against enveloped DNA-containing viruses.

Example 4

The study of antiviral action on an enveloped RNA-containing virus of hepatitis C, belonging to the Flaviviridae family and causing diseases in humans, dogs and primates.

The antiviral agent was used in the form of a 0.5% aqueous solution. The virus dwell time with the solution was 0.5-4.0 minutes at the temperature of 20±2° C.

The viruses of hepatitis C were grown in cell culture. Antiviral activity was determined by the method of inactivation on the surface of artificial leather. A neutralizer (bovine serum) was used in the experiments. The virus reproduction in cells was evaluated by virus-induced cytopathic effect by the degree of inhibition of the infectious virus titer, measured in lg $TCID_{50}$. To work with the hepatitis C virus the pig embryo kidney cell culture (PEK) was used.

The findings on virucidal activity of the antiviral solution during treatment of the test objects infected with hepatitis C virus with a 0.5% solution, are presented in Table 5.

Thus, the tested antiviral solution exhibits virucidal activity against enveloped RNA-containing virus of hepatitis C.

Example 5

The study of antiviral action of the antiviral agent on enveloped RNA-containing human immunodeficiency viruses. Human immunodeficiency viruses of various serotypes cause infectious diseases in humans and animals (monkeys).

To work with the human immunodeficiency virus human lymphoblastoid MT-4 cells were used. The virus reproduction in cells was evaluated by virus-induced cytopathic effect by the degree of inhibition of the infectious virus titer, measured in lg $TCID_{50}$.

The antiviral agent was used in the form of a 1.0% aqueous solution. The virus dwell time with the solution was 0.5-4.0 minutes at the temperature of 20±2° C.

The findings on virucidal activity of the antiviral solution during treatment of the test objects infected with the human immunodeficiency virus with a 1.0% solution, are presented in Table 6.

Thus, the tested antiviral solution exhibits virucidal activity against enveloped RNA-containing virus of human and animal immunodeficiency.

Example 6

The study of antiviral action of the antiviral agent on an enveloped RNA-containing influenza A virus causing diseases in humans and animals (birds, pigs, horses).

The antiviral agent was used in the form of a 0.5% aqueous solution. The virus dwell time with the solution was 0.5-4.0 minutes at the temperature of 20±2° C.

The viruses were grown in cell culture. Antiviral activity was determined by the method of inactivation on the surface of artificial leather. A neutralizer (bovine serum) was used in the experiments. The virus reproduction in cells was evaluated by virus-induced cytopathic effect by the degree of inhibition of the infectious virus titer, measured in lg $TCID_{50}$. To work with the influenza A virus canine kidney cells (MDCK) were used.

The findings on virucidal activity of the antiviral solution during treatment of the test objects infected with influenza A virus with a 0.5% solution, are presented in Table 7.

Thus, the tested antiviral solution exhibits virucidal activity against enveloped RNA-containing influenza virus causing diseases in humans and animals.

Example 7

The Antiviral Agent's Activity Against Bacterial Viruses (Bacteriophages)

A commercial complex of bacterial viruses used for treating intestinal infections caused by *Shigella, Escherichia, Salmonella Proteus, Pseudomonas Staphylococcus* bacteria genera was used for the study.

The testing was performed on *Shigella flexneri* 2a VT-13-678. *P. aeruginosa* VT-900, *P. vulgaris* VT-12-445 *S. aureus* VT-209 strain. Bacteriophages were placed into a 0.5% solution of the antiviral agent for 60 seconds, deposited on Millipore filters, washed with isotonic sodium chloride solution, after which the bacteriophages were washed away and their titer was determined by the agar layers method.

Thus, a complete inactivation of the used mixture of viruses-bacteriophages takes place in one minute.

The results of the bacterial viruses treatment with the antiviral agent are shown in Table 8.

Example 8

The vast majority of plant viruses are non-enveloped RNA-containing viruses. So is the Potato Virus X used in the study (Potato virus X, PVX).

The potato viruses were placed into a 1.0% solution of the antiviral agent for 60 seconds, deposited on Millipore filters, washed with isotonic sodium chloride solution, after which the viruses were washed away, the cells were prepared and infected under the conditions of a microclonal propagation in vitro.

During the first cutting, an analysis for incidence of virus by the enzyme immunodetection method with fixation of the analyze results by photometer was carried out. The results showed that treatment of the Potato Virus X with the antiviral agent completely inhibits viral infection.

The test results showed that the claimed solution possesses a virucidal activity against various, including unrelated non-enveloped and enveloped, DNA and RNA-containing viruses in human, animals, plants and bacteria.

The results on incidence of the virus are shown in Table 9.

The results showed that treatment of the Potato Virus X with the antiviral agent completely inhibits viral infection.

The test results showed the claimed solution possesses a virucidal activity against various, including unrelated non-enveloped and enveloped, DNA and RNA-containing viruses in human, animals, plants and bacteria.

INDUSTRIAL APPLICABILITY

The invention is implemented using common materials and equipment, resulting, according to the applicant's opinion, in compliance of the invention with the "Industrial Applicability" ("IA") criterion for patentability.

TABLE 1

Characteristics of the substance preparation according to Example 3.

| Ex. No. | Reaction temperature, ° C. | Reaction time, h | Average molecular weight of the product, (formula) | Elemental analysis data, % | | | |
|---|---|---|---|---|---|---|---|
| | | | | C | H | N | C |
| 1 | 190 | 0.5 | 2544 ($C_{95}H_{224}Cl_{15}N_{46}$) | 44.71 | 8.83 | 25.48 | 20.98 |
| 2 | 210 | 1 | 13445 ($C_{505}H_{1171}Cl_{80}N_{241}$) | 45.0 | 8.79 | 25.17 | 21.08 |
| 3 | 210 | 4.5 | 26769 ($C_{1010}H_{2339}Cl_{160}N_{481}$) | 45.03 | 8.77 | 25.08 | 20.09 |

TABLE 2

The findings on virucidal activity of the solution during treatment of the test objects infected with the poliomyelitis virus with a 1.0% solution of the antiviral agent.

| Test | Disinfection time, min | Degree of inhibition, lg $TCID_{50}$ | Method of treatment |
|---|---|---|---|
| Artificial leather | 0.5 | 3.2 | Wiping |
| | 1.0 | 4.0 | |
| | 2.0 | 4.5 | |
| | 2.5 × 2 times | 4.5 | |

TABLE 3

The findings on virucidal activity of the antiviral solution during treatment of the test objects infected with the adenoviruses with a 0.5% solution.

| Test | Disinfection time, min | Degree of inhibition, lg $TCID_{50}$ | Method of treatment |
|---|---|---|---|
| Artificial leather | 0.5 | 3.4 | Wiping |
| | 1.0 | 4.0 | |
| | 2.0 | 4.0 | |
| | 1.5 × 2 times | 4.0 | |

TABLE 4

The findings on virucidal activity of the antiviral solution during treatment of the test objects infected with herpes simplex virus with a 1.0% solution.

| Test | Disinfection time, min | Degree of inhibition, lg TCID$_{50}$ | Method of treatment |
|---|---|---|---|
| Suspension test | 1.0 | 1.0 | Mixing, virus:solution (1:9) |
| Artificial leather | 0.5 | 2.0 | Wiping |
|  | 1.0 | 2.5 |  |
|  | 2.0 | 3.0 |  |
|  | 1.5 × 2 times | 4.0 |  |

TABLE 5

The study of virucidal activity of the solution in the course of treatment of the test objects infected with the hepatitis C virus with a 0.5% solution.

| Test | Disinfection time, min | Degree of inhibition, lg TCID$_{50}$ | Method of treatment |
|---|---|---|---|
| Suspension test | 0.5 | 3.5 | Mixing, virus:solution (1:9) |
|  | 1.0 | 4.5 |  |
| Artificial leather | 1.0 | 4.2 | Wiping |

TABLE 6

The study of virucidal activity of the solution in the course of treatment of the test objects infected with the human immunodeficiency virus with a 1.0% solution.

| Test | Disinfection time, min | Degree of inhibition, lg TCID$_{50}$ | Method of treatment |
|---|---|---|---|
| Suspension test | 1.0 | 3.5 | Mixing, virus:solution (1:9) |
| Artificial leather | 0.5 | 4.0 | Wiping |
|  | 1.0 | 4.0 |  |
|  | 2.0 | 4.5 |  |
|  | 1.5 × 2 times | 5.0 |  |

TABLE 7

The study of virucidal activity of the solution in the course of treatment of the test objects infected with the influenza A virus with a 0.5% solution.

| Test | Disinfection time, min | Degree of inhibition, lg TCID$_{50}$ | Method of treatment |
|---|---|---|---|
| Suspension test | 1.0 | 4.0 | Mixing, virus:solution (1:9) |
| Artificial leather | 1.0 | 4.2 | Wiping |
|  | 2.0 | 4.7 |  |
|  | 1.5 × 2 times | 5.0 |  |

TABLE 8

Treatment of bacterial viruses with the antiviral agent.

| Test microbe | Virus titer before treatment | Virus titer in 30 seconds of exposure | Virus titer in 60 seconds of exposure |
|---|---|---|---|
| *Shigella flexneri* 2a | $10^5$/ml | 10 | 0 |
| *P. aeruginosa* VT-900 | $10^5$/ml | 10 | 0 |
| *P. vulgaris* VT-12-445 | $10^4$/ml | 0.5 | 0 |
| *S. aureus* VT-209 | $10^6$ ml | 40 | 0 |

TABLE 9

Incidence of the virus.

| Test plant | Absorbance at 490 nm | |
|---|---|---|
|  | 7 days | 14 days |
| Positive control | 0.09 | 0.850 |
| Negative control | 0.07 | 0.09 |
| Antiviral agent | 0.07 | 0.08 |

The invention claimed is:

1. A method of treating a viral infection in a subject in need thereof, the method comprising administering to the subject an effective amount of a compound comprising the structure $$\left[\underset{H}{\overset{}{N}}-\underset{H}{\overset{}{N}}\left[\overset{NH}{\overset{\|}{C}}-\underset{H}{\overset{H}{N}}\diagup\diagdown\diagup\diagdown\underset{H}{\overset{}{N}}\overset{NH}{\overset{\|}{C}}\right]_n-NH_2\right]_m \cdot (n+1) \cdot m\,HX,$$

or a pharmaceutically acceptable salt thereof, wherein HX is an acid; n is 3-20; and m is 4-20.

2. The method of claim 1, wherein n is 5 and m is 6.
3. The method of claim 1, wherein n is 10 and m is 10.
4. The method of claim 1, wherein the infection is caused by a virus selected from the group consisting of: poliovirus; adenovirus; herpes virus; hepatitis C; immunodeficiency virus; influenza A virus; bacterial virus; and potato virus X.
5. The method of claim 1, wherein the infection is an infection of the respiratory organs, intestine, eye or lymphoid tissue.
6. The method of claim 1, wherein said viral infection is an infection of the respiratory organs.
7. The method of claim 1, wherein the compound is administered by topical administration.
8. A method of inhibiting a virus, comprising contacting the virus with an effective amount of a compound comprising the structure $$\left[\underset{H}{\overset{}{N}}-\underset{H}{\overset{}{N}}\left[\overset{NH}{\overset{\|}{C}}-\underset{H}{\overset{H}{N}}\diagup\diagdown\diagup\diagdown\underset{H}{\overset{}{N}}\overset{NH}{\overset{\|}{C}}\right]_n-NH_2\right]_m \cdot (n+1) \cdot m\,HX,$$

or a pharmaceutically acceptable salt thereof, wherein HX is an acid; n is 3-20; and m is 4-20.

9. The method of claim 7, wherein n is 5 and m is 6.
10. The method of claim 7, wherein n is 10 and m is 10.
11. The method of claim 7, wherein the virus selected from the group consisting of: poliovirus; adenovirus; herpes virus; hepatitis C; immunodeficiency virus; influenza A virus; bacterial virus; and potato virus X.
12. The method of claim 7, wherein the virus is present on the surface of a structure.

13. A method of treating a viral infection in a subject in need thereof, the method comprising administering to the subject an effective amount of an antiviral agent, the antiviral agent consisting essentially of the compound

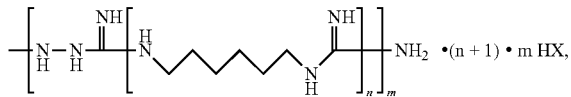

or a pharmaceutically acceptable salt thereof, wherein HX is an acid; n is 3-20; and m is 4-20.

14. The method of claim 13, wherein the antiviral agent consists of the compound

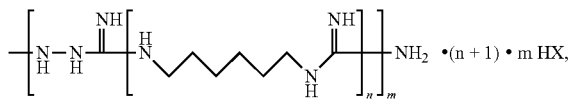

or a pharmaceutically acceptable salt thereof, wherein HX is an acid; n is 3-20; and m is 4-20.

15. The method of claim 13, wherein n is 5 and m is 6.

16. The method of claim 13, wherein n is 10 and m is 10.

17. The method of claim 13, wherein the infection is caused by a virus selected from the group consisting of: poliovirus; adenovirus; herpes virus; hepatitis C; immunodeficiency virus; influenza A virus; bacterial virus; and potato virus X.

18. The method of claim 13, wherein the infection is an infection of the respiratory organs, intestine, eye or lymphoid tissue.

19. The method of claim 13, wherein said viral infection is an infection of the respiratory organs.

20. The method of claim 13, wherein the compound is administered by topical administration.

* * * * *